(12) United States Patent
Padmanabhan (10) Patent No.: US 12,161,752 B2
(45) Date of Patent: Dec. 10, 2024

(54) COMPOSITIONS AND METHODS FOR THE TREATMENT OF ANTERIOR BLEPHARITIS AND POSTERIOR BLEPHARITIS

(71) Applicant: Vishwanath Padmanabhan, Singapore (SG)

(72) Inventor: Vishwanath Padmanabhan, Singapore (SG)

( * ) Notice: Subject to any disclaimer, the term of this patent is extended or adjusted under 35 U.S.C. 154(b) by 825 days.

(21) Appl. No.: 16/997,079

(22) Filed: Aug. 19, 2020

(65) Prior Publication Data
US 2021/0052490 A1  Feb. 25, 2021

Related U.S. Application Data

(60) Provisional application No. 62/889,323, filed on Aug. 20, 2019.

(51) Int. Cl.
| | | |
|---|---|---|
| *A61K 9/00* | (2006.01) | |
| *A61K 31/7048* | (2006.01) | |
| *A61K 47/10* | (2017.01) | |
| *A61K 47/18* | (2017.01) | |
| *A61K 47/22* | (2006.01) | |
| *A61K 47/38* | (2006.01) | |
| *A61K 9/08* | (2006.01) | |

(52) U.S. Cl.
CPC ........ *A61K 9/0048* (2013.01); *A61K 31/7048* (2013.01); *A61K 47/10* (2013.01); *A61K 47/183* (2013.01); *A61K 47/22* (2013.01); *A61K 47/38* (2013.01); *A61K 9/08* (2013.01)

(58) Field of Classification Search
None
See application file for complete search history.

(56) References Cited

U.S. PATENT DOCUMENTS

| | | |
|---|---|---|
| 8,415,311 B2 | 4/2013 | Manetta et al. |
| 9,782,425 B2 | 10/2017 | Jacovella et al. |
| 2009/0061025 A1 | 3/2009 | Gao et al. |
| 2013/0224272 A1 | 8/2013 | Gao |
| 2017/0232024 A1* | 8/2017 | Tan .................. A61K 47/34 514/30 |

FOREIGN PATENT DOCUMENTS

| | | |
|---|---|---|
| CN | 101272796 A | 9/2008 |
| EP | 1933849 * | 6/2008 |
| JP | 2009510049 A | 3/2009 |
| JP | 2010538011 A | 12/2010 |
| JP | 2018530548 A | 10/2018 |
| RU | 2008117148 A | 11/2009 |
| WO | WO2005058312 A1 | 6/2005 |
| WO | WO2006119174 A1 | 11/2006 |
| WO | 2007054822 A2 | 10/2007 |
| WO | 2016022066 A1 | 2/2016 |
| WO | WO2016141182 A1 | 9/2016 |
| WO | 2017055295 A1 | 4/2017 |
| WO | 2020077284 A1 | 4/2020 |

OTHER PUBLICATIONS

A diversity of GABA receptors in the retina. Peter D.Lukasiewicz, Colleen R.Shields Seminars in Cell & Developmental Biology, Jun. 1998, pp. 293-29, vol. 9, Issue 3.
US Pharmacopela <797> Pharmaceutical Compounding—Sterile Preparations Reprinted from USP42-NF37 (last revised 2008).
Microbial and immunological investigations of chronic non-ulcerative blepharitis and meibomnianitis. D V Seal et al Br J Ophthalmol. Aug. 1985; 69(8):604-11.
Lid flora in blepharitis. LR Groden et al Cornea Jan. 1991; 10(1):50-3.
Treatment of blepharitis: recent clinical trials. Stephen C Pflugfelder 1, Paul M Karpecki 2, Victor L Perez 3 Ocul Surf Oct. 2014; 12(4):273-84.
Intense Pulsed Light Therapy with Optimal Pulse Technology as an Adjunct Therapy for Moderate to Severe Blepharitis-Associated Keratoconjunctivitis. Ruan F, Zang Y, Sella R, Lu H, Li S, Yang K, Jin T, Afshari NA, Pan Z, Jie Y. J Ophthalmol. Sep. 16, 2019; 2019:3143469.
Safety and efficacy of 4-terpineol against microorganisms associated with blepharitis and common ocular diseases. Su CW, Tighe S, Sheha H, Cheng AMS, Tseng SCG. BMJ Open Ophthalmol. Jun. 4, 2018;3(1):e000094. doi: 10.1136/bmjophth-2017-000094. eCollection 2018.
The International Workshop on Meibomian Gland Dysfunction: Executive Summary. Kelly K. Nichols et al. Investigative Ophthalmology & Visual Science, Special Issue 2011, vol. 52, No. 4.
Drug bioavailability from topically applied ocular drops. Does drop size matter? Anselm G.M. Junemann et al. Ophthalmol J 2016; 29-35, vol. 1, No. 1.
A Comprehensive Insight on Ocular Pharmacokinetics. Vibhuti Agrahari et al. Drug Deliv Transl Res Dec. 2016; 6(6): 735-754.
Ivermectin to reduce malaria transmission I. Pharmacokinetic and pharmacodynamic considerations regarding efficacy and safety. Chaccour et al. Malar J (2017) 16:161.
Topical Drug Delivery to the Posterior Segment of the Eye: Addressing the Challenge of Preclinical to Clinical Translation. Gerard A. Rodriguez et al. Pharm Res (2018) 35:245.
Christopher M. Putnam, Diagnosis and management of blepharitis: an optometrist's perspective, Clinical Optometry 2016:8 71-78.
Highlights of Prescribing Information for Soolantra, Published Dec. 2014 by the U.S. Food and Drug Administration, pp. 1-8.

(Continued)

*Primary Examiner* — Genevieve S Alley
(74) *Attorney, Agent, or Firm* — Ashok Tankha (57) ABSTRACT

Disclosed herein are pharmaceutical compositions and methods for the treatment of anterior blepharitis and posterior blepharitis which may be of primary origin and not secondary to other factors such as infections, infestations or rosacea. The composition comprises Ivermectin in the range of about 0.001% to 20% by weight of the total composition. Topical administration of said compositions precisely to the eyelid margin provides therapeutic benefit to patients suffering from anterior blepharitis and posterior blepharitis.

15 Claims, 7 Drawing Sheets

(56) References Cited

OTHER PUBLICATIONS

M. Schaller, Dual anti-inflammatory and anti-parasitic action of topical ivermectin 1% in papulopustular rosacea, Journal of the European Academy of Dermatology and Venerology, vol. 31, pp. 1907-1911.

M. Schaller, L. Gonser, K. Belge. C. Braunsdorf, R. Nordin, A. Scheu, C. Borelli, , Dual anti-inflammatory and anti-parasitic action of topical ivermectin 1% in papulopustular rosacea, European Academy of Dermatology and Venereology, 2017, 31, pp. 1907-1911, DOI: 10.1111/jdv.14437.

Christopher M Putnam, Diagnosis and management of blepharitis: an optometrist's perspective, Clinical Optometry, Aug. 2016, pp. 71-78.

* cited by examiner

COMPOSITIONS AND METHODS FOR THE TREATMENT OF ANTERIOR BLEPHARITIS AND POSTERIOR BLEPHARITIS

CROSS-REFERENCE TO RELATED APPLICATIONS

This application claims priority to and the benefit of the provisional patent application titled "A Method Of Treatment For Anterior And Posterior Blepharitis", application No. 62/889,323, filed in the United States Patent and Trademark Office on Aug. 20, 2019. The specification of the above referenced patent application is incorporated herein by reference in its entirety.

FIELD OF THE INVENTION

The present invention relates to pharmaceutical compositions and methods for the treatment of anterior blepharitis and posterior blepharitis which may be of primary origin and not secondary to other factors such as infections, infestations or rosacea. The compositions comprise Ivermectin in the range of 0.001% to 20% by weight of the total composition. Topical administration of said compositions precisely to the eyelid margin provides therapeutic benefit to patients suffering from anterior blepharitis and posterior blepharitis.

BACKGROUND

Figure 1A:
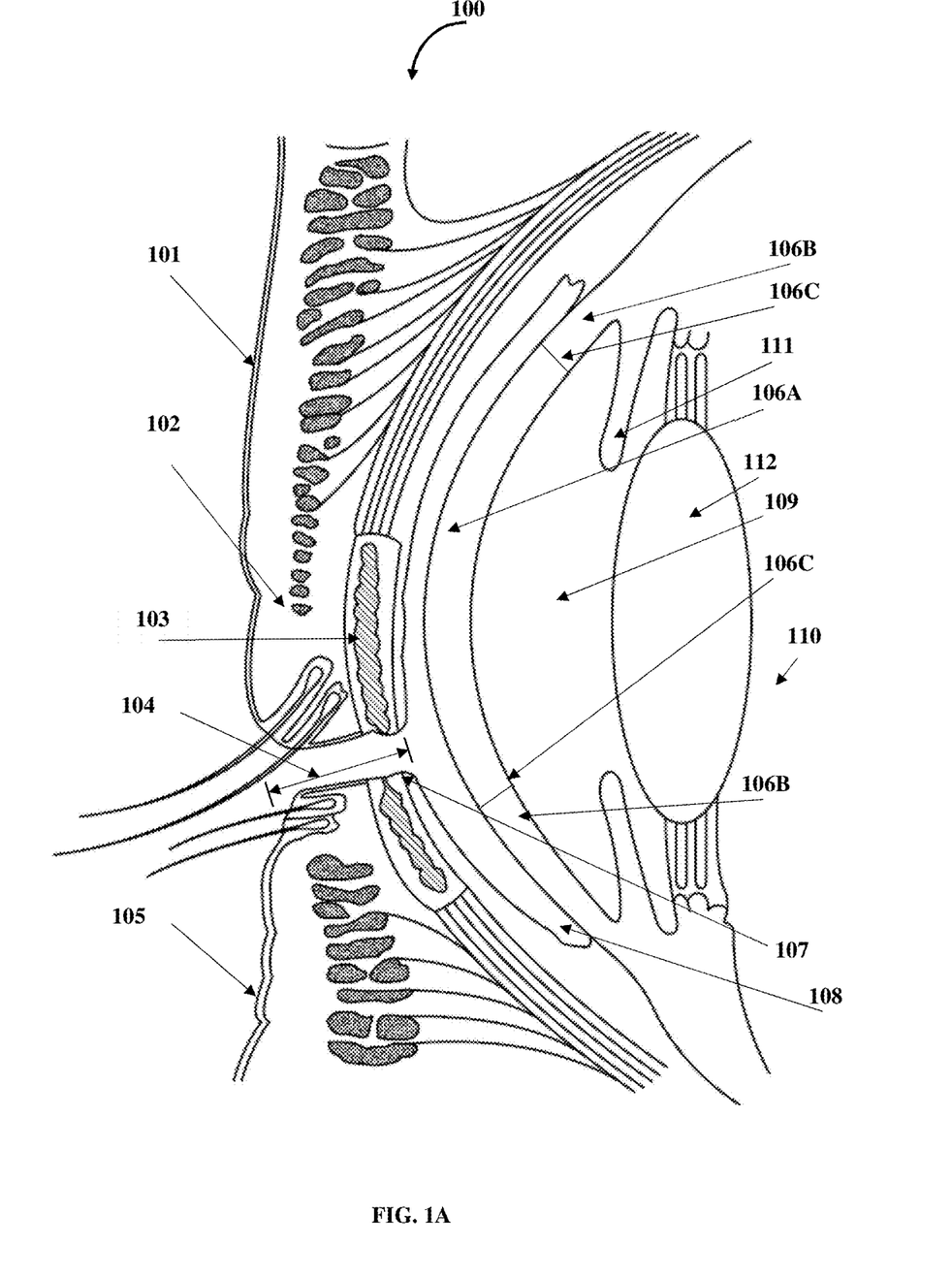
FIG. 1A illustrates the section of anterior part of eye (A sagittal section through the anterior part of the eyeball and eyelids).

FIG. 1A illustrates a sagittal section through the anterior part of eyeball and the eyelids 100. Blepharitis is the term used to describe inflammatory conditions of eyelid margins 104 extending from the area around the roots of the anterior most eyelash roots proximally to the edge of the lid margin 104 distally that contacts the eyeball 106. Blepharitis is a disease with multifactorial origins which are to date poorly understood. It is the most common form of disease affecting the eyelids and accounts for the majority of presentations for consulting from Ophthalmologists. In its most common presentation, the cause is unknown. It is a chronic inflammatory condition which causes multiple symptoms such as ocular discomfort, itching, redness, foreign body sensation, dry eye disease, lid margin 104 swelling and blurring of vision by causing breakdown of the tear film lining the eyeball.

Various classifications of blepharitis have been proposed but none of these have individually gained widespread acceptance and often tend to be used together as well as interchangeably.

Figure 1B:
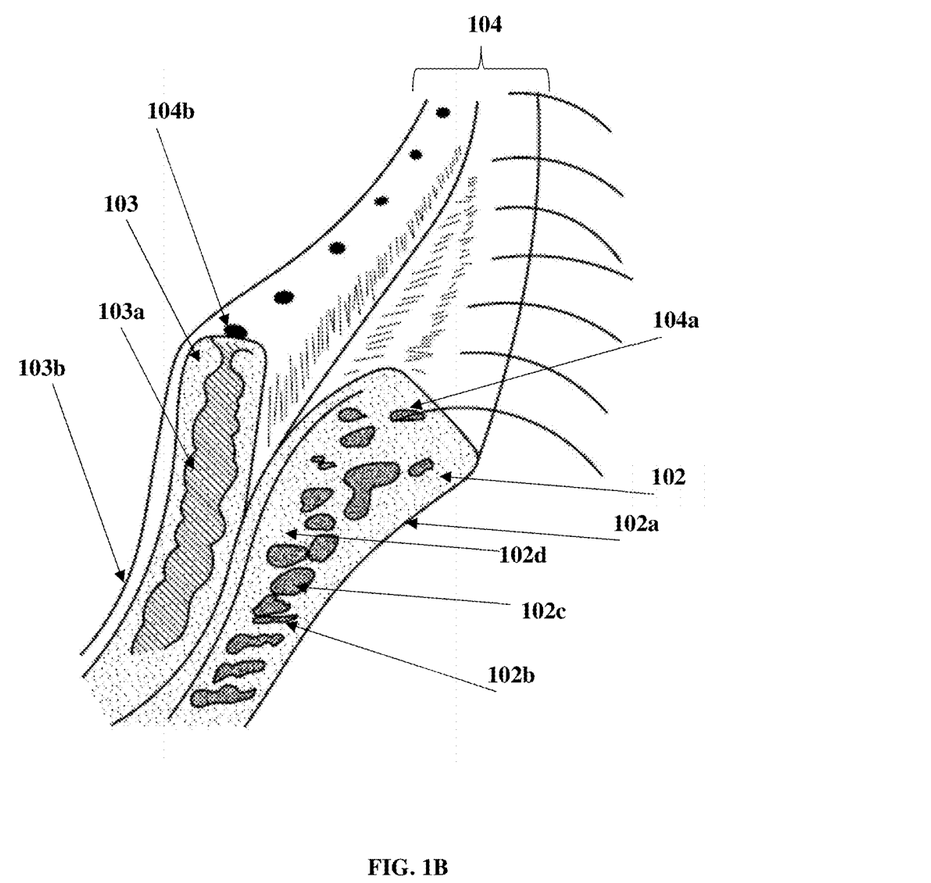
FIG. 1B illustrates a close-up of the eyelid margin (artificially split between the anterior and posterior lamellae).

Clinically, classification on anatomical grounds is as follows:

Anterior blepharitis occurs at the outside front edge of the eyelid where the eyelashes attach and which affects the roots of the eyelashes, follicles, and keratinized skin around them, as shown in FIG. 1B. The roots of the eyelashes apart from containing lash bulbs, also contain sebaceous glands.

Posterior blepharitis affects the inner edge of the eyelid that touches the eyeball 106. It affects the Meibomian glands 103A which are located within the body of the tarsal plate 103 and their openings 104B on lid margin 104 and the epithelium around them, as shown in FIG. 1B. This is also often termed Meibomitis or Meibomian Gland Disease (MGD).

Classification according to etiology is also commonly used clinically. This classification is as follows:

Primary blepharitis which is a condition of as yet uncertain etiology and Secondary blepharitis where the cause of the pathology may be due to infection with bacteria, infestation with lice or mites, systemic conditions such as psoriasis, rosacea, atopic disease, drugs such as Isotretinoin.

The vast majority of the blepharitis cases that present clinically do not have any obvious causative factors and are therefore termed Primary or non-infective blepharitis. The prevalence of this condition is very high and estimates range from 10% to over 90% of the general population. The prevalence increases with age and ethnicity, being more common in East Asian populations. It remains a poorly understood and treated clinical entity despite being one of the most common conditions that present to a clinical practitioner.

FIG. 1A also illustrates a corneo-scleral junction 106c, a posterior-chamber of the eye (vitreous cavity) and the neural retinal lines 110 in the inner wall of the posterior chamber, the iris with the pupil as the central aperture 111, and the crystalline lens which forms the border between the anterior and posterior chambers 112.

Figure 1C:
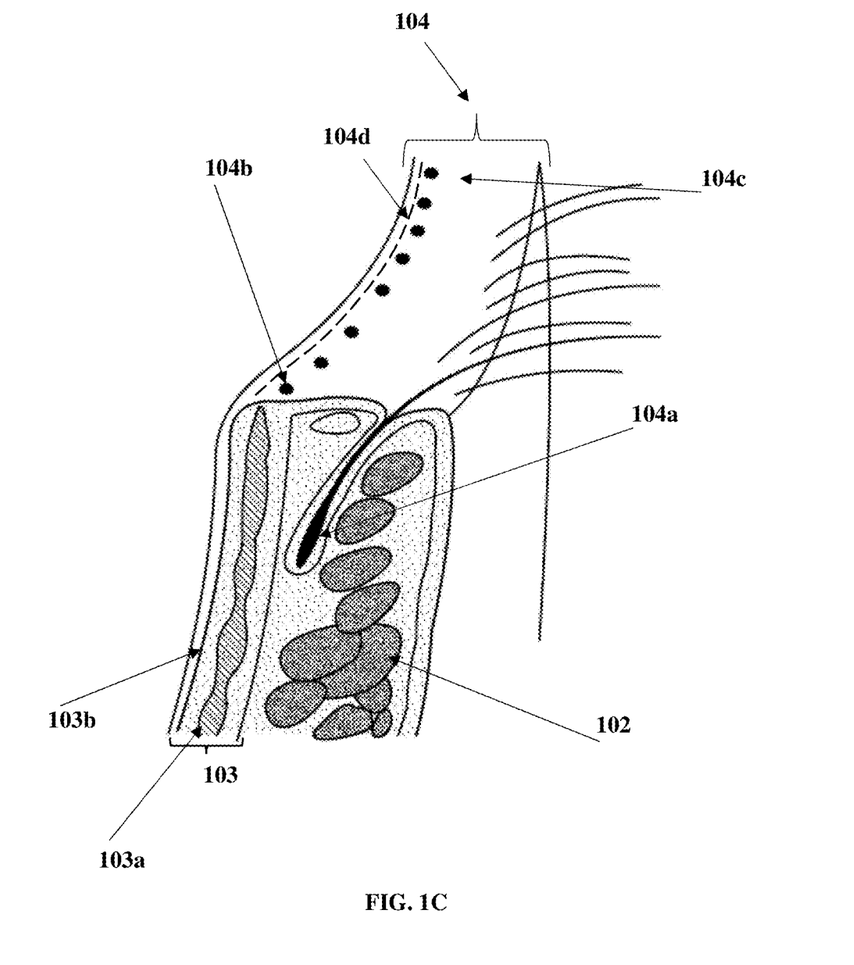
FIG. 1C illustrates a close up of the eyelid margin showing the relevant areas and structures affected by anterior blepharitis and posterior blepharitis (without artificially splitting the anterior and the posterior lamellae).

FIG. 1B illustrates a close up of eyelid margin 104 (artificially split between anterior 102 and posterior lamellae 103. FIG. 1B illustrates the skin 102A connective tissue 102B muscle 102C, and fat 102D, of the anterior lamella 102. FIG. 1C illustrates a close up of the eyelid margin 104 showing relevant area and structures affected by anterior blepharitis and posterior blepharitis. The relevant area and structures affected by anterior blepharitis and posterior blepharitis in the eyelid margin 104 comprise meibomian gland opening 104B, eyelash root 104A, the skin lining 104C the anterior and the posterior lamella 103 (tarsal plate with Meibomian gland) at the lid margin, and the internal tissues of the anterior lamella 102 at the lid margin. Notwithstanding the intricacies of classification, the final pathology common to all cases of primary blepharitis is inflammatory changes in the roots of the eyelashes, the skin of the eyelid margin 104 and the Meibomian glands 103A of the tarsal plate 103 and their openings 104B on the lid margins 104, shown in FIG. 1B and FIG. 1C. It is the inflammatory process that results in the symptoms and signs that characterize the condition. Additionally, despite the anatomical classification into anterior and posterior blepharitis, in practice, the overwhelming majority of cases have varying degrees of inflammation that affect the lid margin 104 of both the anterior lamella 102 and the posterior lamella 103 of the eyelids. Therefore, effective therapy is required that treats the whole extent of the eyelid margin 104.

Figure 3:
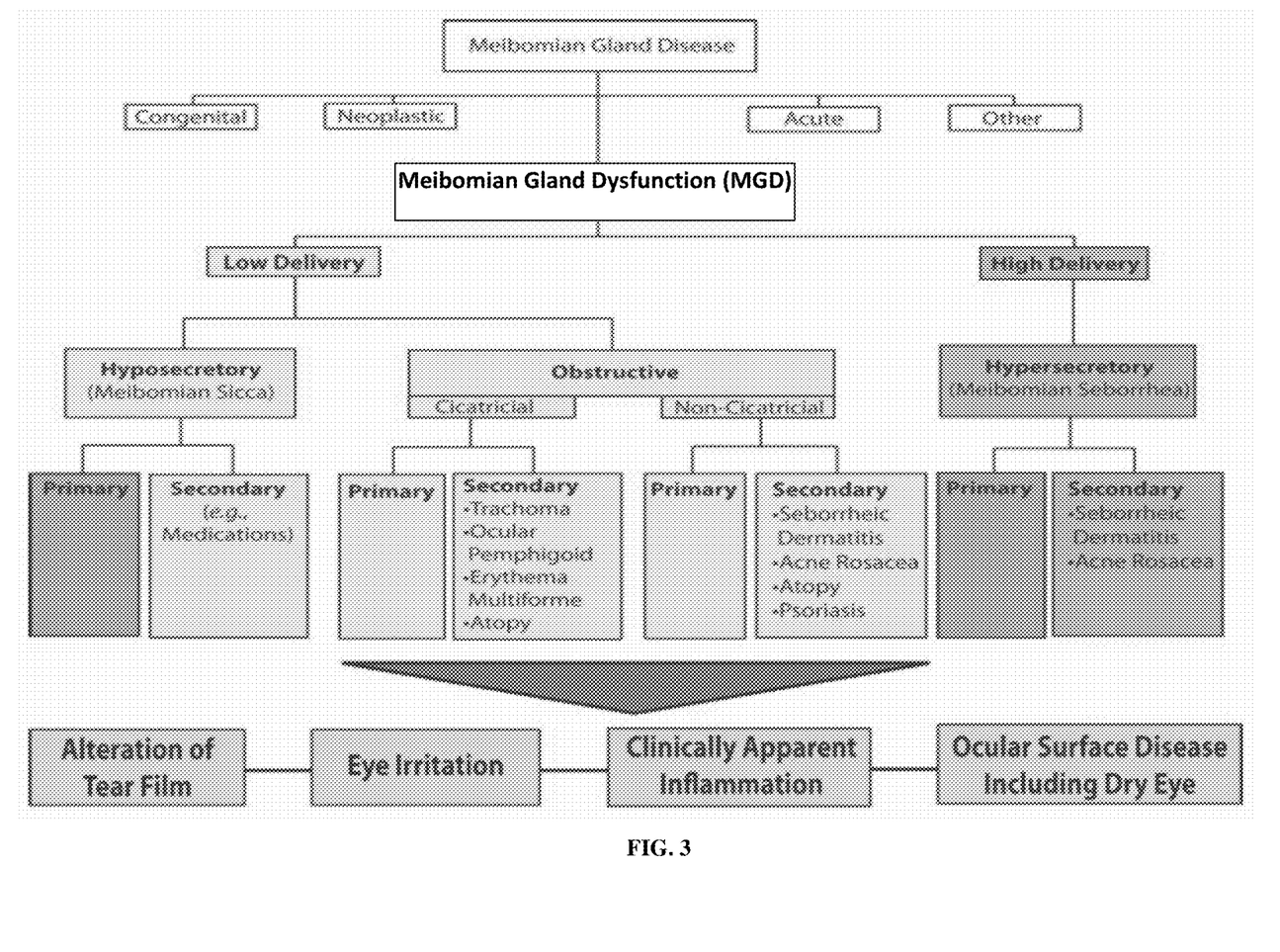
FIG. 3 exemplarily illustrates a classification of various proposed types of Meibomian Gland Dysfunction.

FIG. 3 exemplarily illustrates a classification of various proposed types of Meibomian gland dysfunction, all being sub-classified into primary and secondary forms and all leading to Clinically Apparent Inflammation. This classification into primary and secondary forms would also apply to anterior blepharitis. The ultimate outcome is inflammation which is what leads to most of the symptoms, signs and outcomes of blepharitis. FIG. 3 is reproduced from "The International Workshop on Meibomian Gland Dysfunction: Executive Summary", authored by Kelly K. Nichols et al. and published in *Investigative Ophthalmology & Visual Science*, Special Issue 2011, Vol. 52, No. 4, Pages 1922-1929.

Figure 4:
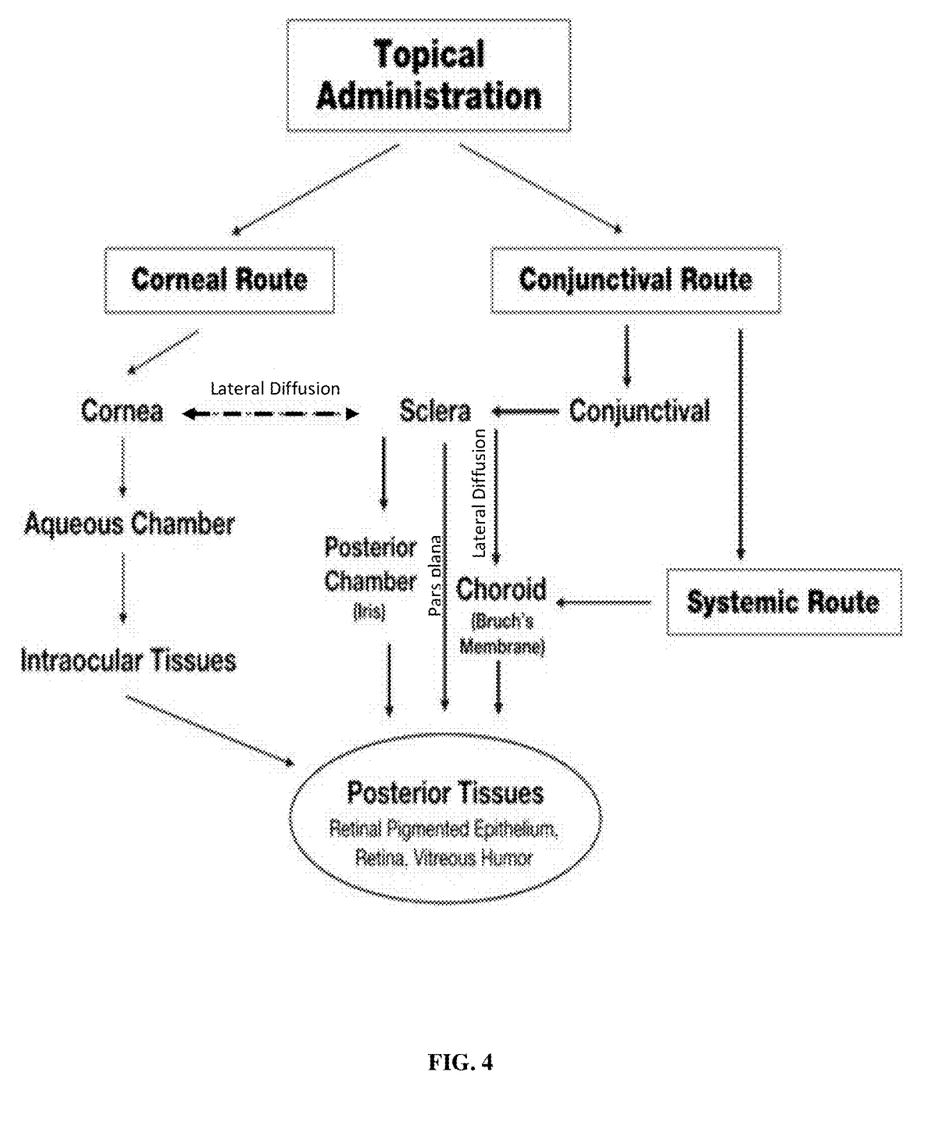
FIG. 4 exemplarily illustrates the drug distribution pathways through the corneal and conjunctival/scleral routes following topical administration.

FIG. 4 exemplarily illustrates the drug distribution pathways through the corneal and conjunctival/scleral routes following topical administration. It provides the pathways through which topical medication that contacts the eyeball can take to reach the posterior neural tissues of the retina and the optic nerve. Therefore, agents that are potentially toxic to the neural tissues of the retina and optic nerve can penetrate into the eye and affect those tissues if they mix with or dissolve in the tear film. FIG. 4 is reproduced from "Topical and systemic drug delivery to the posterior segments", authored by Hughes et al. and published in "*Advanced Drug Delivery Reviews*, 57, (2005), 2010-2032.

Although the etiology of primary blepharitis is as yet unclear, postulations for the causative factors range from overgrowth of the normal commensal bacterial organisms of the eyelid, reactions to toxins secreted by these bacteria, changes in the composition of the sebaceous material secreted by the sebaceous glands of the eyelashes and the Meibomian glands contained in the tarsal plate 103 of the eyelid. While blepharitis is a disease complex with multifactorial etiology, in the most common presentation, the etiology of the inflammatory process is unknown.

Secondary blepharitis is that condition where there is a known causative factor such as obvious microbial infection, lash infestation with mites such as Demodex, rosacea, systemic conditions such as psoriasis, atopic disease, side effects of drugs such as Isotretinoin which is used as treatment for acne vulgaris, chemical injury, post radiation effects and other assorted conditions.

Blepharitis due to infestation of the eyelash roots with mites such as Demodex folliculorum and of the Meibomian glands with Demodex brevis is also considered by some to be a specific entity but this is not widely accepted as a considerable body of evidence indicates that the Demodex infestation may be secondary to the primary inflammatory process. The normal flora of the skin and by extension, the keratinized surfaces of the lid margin 104 normally contain various organism including bacteria, fungi and mites as commensal organism necessary to optimize the ecology of the skin. Demodex species are very common commensals and their identification increases with age with some reports indicating that they are present in up to 30% of eyelash specimens. The average rate of infestation of eyelash specimens with Demodex folliculorum is around 30% in cases of inflammatory blepharitis which is almost identical to the rate of infestation found in eyelash specimens of subjects without blepharitis. Therefore, the role of Demodex species in the etiology of even some subsets of blepharitis and especially Meibomian gland disease remains speculative. Therefore, the vast majority of cases comprise blepharitis due to inflammation of unknown etiology.

Current methods for treating this condition have met with limited success. They comprise predominantly lid margin 104 cleansing measures where the lid margin 104 is scrubbed with various solutions such as shampoos, liquid cleansers and T-tree oil. T-tree oil cleansers comprising the active ingredient called 'Terpinol' have been described as a treatment for presumed Demodex related blepharitis.

Oral pharmaceuticals such as antibiotics such as tetracyclines and macrolytic lactones such as Azithromycin have been proposed but these require daily intake for months. The success of such treatments remains limited. Oral Vitamin D has also been proposed, again with limited success.

Application of topical therapeutic agents to the lid margins 104 for treatment of inflammatory blepharitis includes antibiotics such as tetracyclines, Azithromycin and steroid preparations.

*Investigative Ophthalmology & Visual Science*, Special Issue 2011, Vol. 52, No. 4, 2050-2064, (The International Workshop on Meibomian Gland Dysfunction: Report of Subcommittee on Management and Treatment of Meibomian Gland Dysfunction) provides, Current practice patterns such as Artificial lubricant application, Topical lipid supplementation, Lid Hygiene, Warm compress, Heat application, Topical antibiotic application, Topical steroid application, Topical Calcineurin Inhibitors and Cyclosporin, Systemic administration of Tetracycline and derivatives. It further provides that Demodex mites have an etiologic role in some forms of anterior blepharitis but that there is no evidence for Demodex mites in the etiology of posterior blepharitis.

Application of anti-parasitics such as Ivermectin and Isoxazoline has been suggested as treatment for blepharitis due to presumed infestation by Demodex mites. However, the majority of cases of inflammatory blepharitis are not related to the activity of mites.

Ivermectin is a member of the avermectin class of macrolides which has been used as an antimiticidal agent. Ivermectin is a semi-synthetic compound derived from the fermentation of *Streptomyces avermilitis*. It is a mixture containing 5-O-demethyl-22,23-dihydroavermectin $A_{1a}$ and 5-O-demethyl-25-de(1-methylpropyl)-25-(1-methylethyl)-22,23 dihydroavermectin $A_{1a}$.

Anti-parasitics such as Ivermectin and Isoxazoline are potentially very toxic to certain neural tissues such as the retina which is predominantly composed of neural tissue. The vertebrate and especially the human retina contains neural cells such as the Amacrine cells that contain ligand gated ion channels especially on the GABA (gamma-aminobutyric acid) receptors that are present on neural cells in the retina. GABA is a major inhibitory neurotransmitter in the vertebral retina and plays a major role in the processing of visual information in the retina. There are 3 families of GABA receptors in the retina. These are the ionotropic GABA-A, the ionotropic GABA-C and the metabotropic GAB A-B receptors.

Ivermectin blocks synaptic transmission by cells containing GABA receptors by binding to the ligand gated ion channels in these receptors. This blockage of synaptic transmission results in hyperpolarization of these cells as GABA is a major inhibitory neurotransmitter.

Oral Ivermectin has been shown to have a good safety profile but high doses have caused paralysis as would be expected by the potentiation of inhibition due to hyperpolarization of cells containing inhibitory neurotransmitters. As vertebrates contain GABA mediated tissue only in selected neural tissues such as the Central Nervous System and the retina, the existence of the Blood Brain Barrier and the Blood Retinal Barrier in vertebrates prevents the Ivermectin molecule from reaching these tissues in the normal vertebrate with intact barriers.

Application of topical preparations to the lid margin 104 takes the form of creams, ointments and drops which are either solutions or suspensions of the active ingredients. Waxes have been proposed as vehicles for active ingredients to be applied to the eyelid margin 104 which then act as reservoirs for delivery over the surface of the eyeball 106.

The eyelid margin 104 is a unique structure. It extends from the medial to lateral canthi of the eyelids and is of a flat configuration that enables a reasonably watertight seal when the lids are closed. The outer edge of the eyelid margin 104 is of a slightly curved configuration and is lined by keratinized epithelium which is a continuation of the outer eyelid skin. This keratinized epithelium extends to and includes the lining of the external orifices of the Meibomian glands which are holocrine glands contained within the tarsal plate 103 of the eyelids. It also extends into the ampullae of the Meibomian glands. The anterior lamella 102, shown in FIG. 1B, of the eyelid extends approximately halfway of the thickness of the lid margin 104 and is joined to the posterior lamella 103 which comprises the tarsal plate 103 which provides the stiffness for the eyelid. Just past the external orifices of the Meibomian glands 104B the keratinized epithelium gives way to the mucosal epithelium of the conjunctival lining of the inner surface of the eyelids at the mucocutaneous junction 104D. The inner surface of the eyelids is of a sharp configuration and lies flat against the eyeball 106. Chronic lid margin inflammation leads to hyperkeratinization of the eyelid margin 104 causing blockage and plugging of the orifices 104B.

Figure 2:
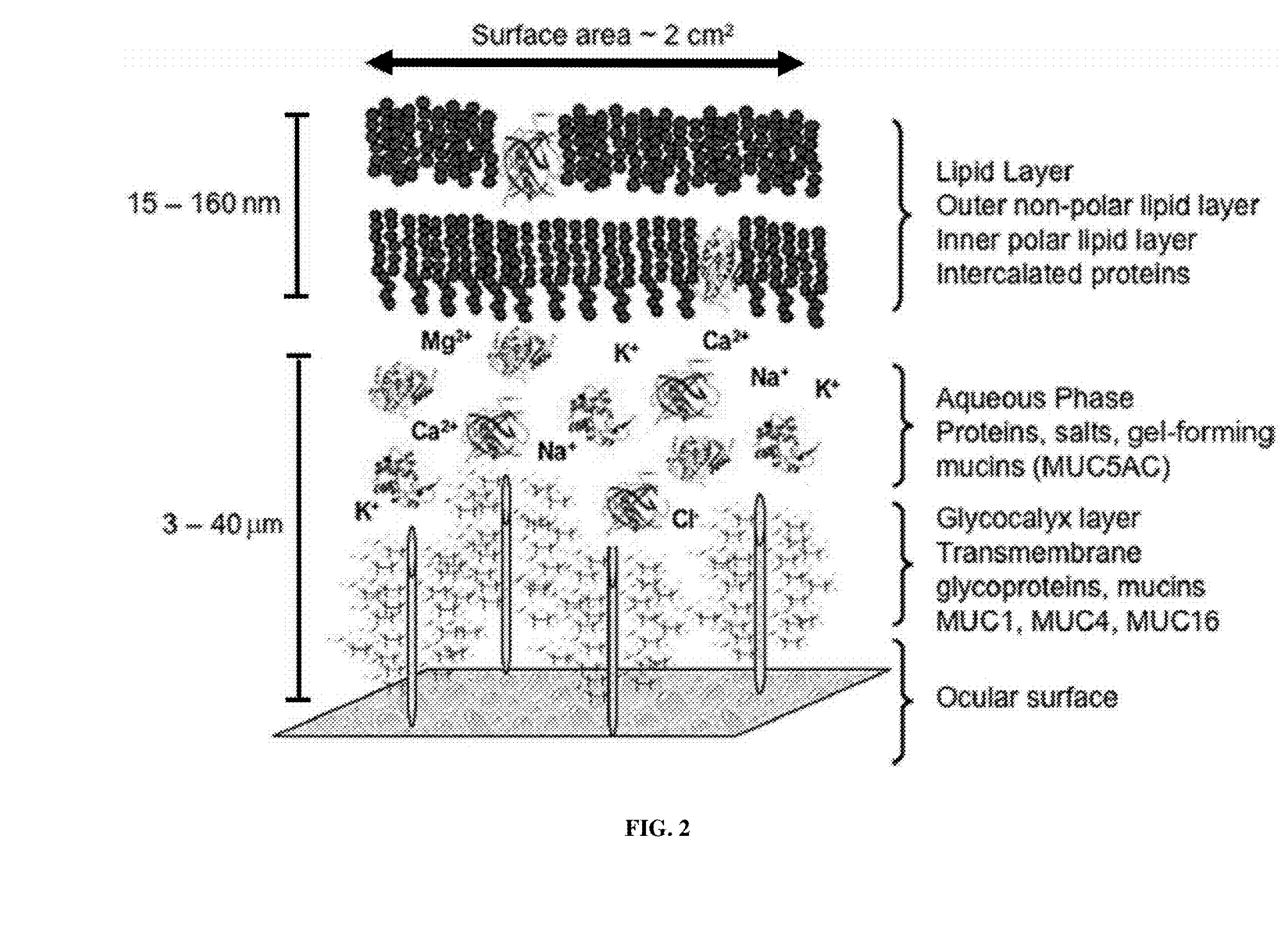
FIG. 2 illustrates a proposed model of the human tear film (not to scale).

Blockage of the Meibomian gland leads to gland dysfunction. The secretions of the Meibomian gland comprise the outer layer of the tear film that lines the eyeball 106. FIG. 2 illustrates a proposed model of the human tear film (not to scale). It provides a cross-section of normal tear film with external lipid layer composed of secretions from Meibomian glands, aqueous phase layer of the tear film secreted by lacrimal gland and mucinous layer secreted by mucous glands of the conjunctiva. This layer lines the epithelium of the cornea and sclera, extending into the conjunctival sac and over the conjunctiva 103b lining the tarsal plate 103. It is limited anteriorly at or near the mucocutaneous junction 104D at the lid margins. The mucinous layer is secreted by specialized cells in the conjunctival epithelium and lines the corneal and conjunctival epithelia directly. It supports the aqueous layer of the tear film by facilitating spreading of the aqueous layer of the tear film. The lipid layer is the outer coat of the tear film and serves to contain the aqueous layer as well as retarding evaporation of the aqueous. The lipid layer is secreted by the Meibomian glands. FIG. 2 is reproduced from "The International Workshop on Meibomian Gland Dysfunction: Executive Summary", authored by Kelly K. Nichols et al. and published in *Investigative Ophthalmology & Visual Science*, Special Issue 2011, Vol. 52, No. 4, Pg 1922-1929.

The tear film comprises 3 layers. The inner layer closest to the eyeball 106 is made up of mucous components. The main bulk of the tear film is an aqueous component secreted by the lacrimal glands. The outer layer of the tear film is a lipid layer comprising fatty and waxy secretions of the Meibomian glands. Chronic inflammation changes the composition of the lipid layer. Blockage of the Meibomian gland orifices reduce the quantities of lipid secreted and enable increased drying out of the aqueous component causing an evaporative dry eye. The lipid layer serves to contain the tear film at the meniscal edge of the tear film at the mucocutaneous junction 104D at the lid margins 104. Therefore, the tear film at the lid margin lies in very close proximity to the orifices of the Meibomian glands, as shown in FIG. 1D.

Figure 1D:
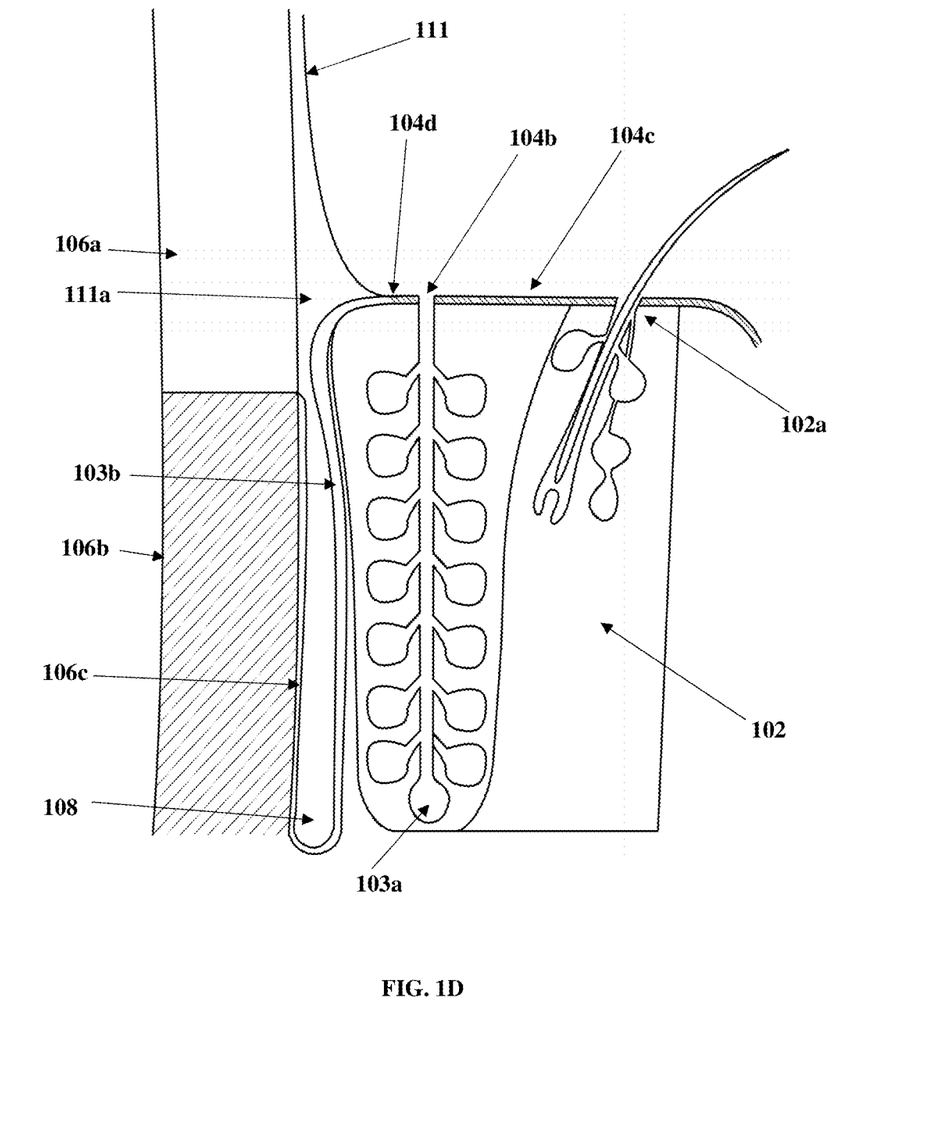
FIG. 1D illustrates a schematic view of the lid margin in relation to the cornea and sclera of the eyeball.

FIG. 1D illustrates a schematic view of the lid margin in relation to the cornea 106A and sclera 106B of the eyeball. In particular, the relationships of the tear film meniscus 111A to the mucocutaneous junction 104D and the orifices of the Meibomian gland. It provides a close up view of the eyelid margin structures in relation to the eyeball which consists of the central transparent cornea 106A and the surrounding non-transparent sclera 106B. The cornea is lined by specialized epithelium (not shown in the diagram) and the sclera 106B is lined by the conjunctival epithelium which is continuous with the conjunctival epithelium which lines the tarsal plates of the posterior lamella 103. The tear film lining the anterior part of the eyeball coats the entire anterior part of the eyeball including the cornea 106A and the sclera 106B. It forms a collection at the junction of where the posterior lid margin contacts the eyeball. This collection takes a meniscal shape. Generally, the anterior edge of the meniscus is at or in the mucoid side of the mucocutaneous junction and the lipid layer of the tear film is supplied to the tear film from the Meibomian gland openings 104B that lie anterior to the meniscal edge.

Existing delivery formulations such as creams, ointments, drops, suspensions, lotions have limited retainability and adhesiveness to the lid margin 104, being prone to dissolving and spreading into the tear film. Drops lotions and solutions are unable to maintain an effective concentration at the desired site of action as they are readily diluted and washed away by the tear film.

Emulsions such as creams and ointments are also prone to being diluted, washed away, accidentally being wiped away, smearing over the eyeball 106 and collecting in the conjunctival Sac 108 of the eyelid.

Apart from the inability of these formulations to maintain an effective concentration at the required site of action, collecting of the active ingredient in the conjunctival sac and smearing over the eyeball 106 will enable the active ingredient to penetrate through the cornea 106A and the sclera 106B of the eyeball 106 and enter into the interior of the eyeball 106 and the inner neural tissues.

Lipophilic molecules can penetrate through the cornea 106 to reach the anterior chamber of the eyeball 109 and subsequently diffuse into the vitreous cavity where they can contact with the neural tissues of the retina that line the vitreous cavity.

Hydrophilic and lipophilic molecules are also able to diffuse through the conjunctiva and sclera especially small molecules of less than 150 kDa. Ivermectin is classified as a small molecule so the possibility of permeating through the conjunctiva and sclera to reach the neuroretina is a real possibility. Neurotoxic agents that dissolve in the tear film and collect in the conjunctival sac 108 present a real possibility of permeating through the conjunctiva and sclera.

Therefore, there is a need for formulations containing active ingredients that can restrict delivery to the immediate area of application. Due to the unique environment of the eyelid margin 104, it should enable accurate application and possess a high degree of retainability both to maximize bioavailability and minimize spread to other areas.

Existing formulations for topical application over bare or hair bearing skin are not suitable as the lid margin is a unique environment that comprises hair bearing skin and skin bordered by an aqueous environment of the tear film, shown in FIG. 1D. It is also subject to the stress placed by closure of the eyelids and the spreading effect of the eyelids during the course of normal blinking.

U.S. Patent Publication No. 2017/0232024 discloses a method of treatment for Demodex related blepharitis where the active ingredient Ivermectin and an antibiotic is formulated in a cream or an ointment which is to be applied using a finger or a cotton bud to the lash roots which lie in the anterior part of the lid margin 104 only. These methods of application are inexact and inaccurate. There is no mention of application over the openings 104B of the Meibomian glands 103A. There is no mention made of treatment of primary blepharitis or of meibomitis or Meibomian gland disease. Additionally, formulation into a pure emulsion such as a cream or an ointment will severely limit adhesiveness and retainability on the lid margin 104. As an example, creams or ointments containing steroid are known to spread to the eyeball 106 and penetrate the ocular coats to enter into the interior of the eyeball. This has been shown to result in adverse effects such as glaucoma, cataract.

U.S. Patent Publication No. 2018/0369184 discloses a method of application of a lipid formulation to the lid margin 104 for delivering a benefit agent to the ocular surface. This formulation is designed specifically to soften or melt at typical eyelid temperatures so that the active ingredient can spread over the ocular surface via the tear film and assisted by the natural spreading effect of blinking.

International Publication No. WO/2007/054822 discloses a method of treating ocular rosacea and blepharitis associated with ocular rosacea using Ivermectin in a topical form. However, blepharitis due to rosacea is a very limited subset of the condition and the preferred formulations are in the form of eyewash or eye drops to be applied to the conjunctival sac 108 of the eye as well as to the cornea 106. These formulations do not specifically target the lid margins 104 and apart from having limited bioavailability due to the diluting effect of the tear film, there is a definite risk of the Ivermectin diffusing into the eyeball 106 and producing toxic effects on the GABA mediated neural cells of the retina.

Therefore, there is a need for an effective and safe method of treating anterior and posterior blepharitis which is of primary origin where the cause is not necessarily related to bacterial infection, presumed mite infestation or other factors that result in blepharitis such as Rosacea, Psoriasis or drugs such as Isotretinoin. Currently available methods of treatment are of limited effectiveness. Formulations currently available for topical application on hair and skin surfaces are not well suited for application on the eyelid margin 104 as it is a unique environment which is very compact and comprises hair and skin and orifices of glands) very closely bordered by an aqueous layer of the tear film (FIG. 1D) and where the tissue is in constant movement as occurs during the act of blinking. There is also a long felt need for a composition that can be applied on the affected areas of the lid margins 104 from around the eyelashes and the adjacent skin to include the keratinized skin 104C between the eyelashes 104A and the mucocutaneous junction 104D of the lid margin and which has some ability to penetrate into the orifices of the Meibomian glands.

SUMMARY OF THE INVENTION

This summary is provided to introduce a selection of concepts in a simplified form that are further disclosed in the detailed description of the invention. This summary is not intended to determine the scope of the claimed subject matter.

The present invention is directed to pharmaceutical compositions and a method for the treatment of the most common form of anterior and posterior blepharitis which may be of primary origin and not secondary to other factors such as infections, infestations or rosacea using such pharmaceutical compositions.

In one aspect, the present invention provides a method for treating anterior blepharitis and posterior blepharitis in a subject in need thereof, comprising topically administering, precisely on eyelid margin of the subject, a pharmaceutical composition comprising Ivermectin and an ophthalmically acceptable carrier without co-administration of another active pharmaceutical ingredient, wherein the pharmaceutical composition comprises 0.001% to 20% (by weight) Ivermectin, and wherein the pharmaceutical composition adheres to the eyelid margin.

In another aspect, the present invention provides a method for treating primary blepharitis in a subject in need thereof, comprising topically administering, once daily for 3 days and repeated once daily for 3 days after 2 weeks, precisely on the eyelid margins of the subject, a pharmaceutical composition comprising Ivermectin and an ophthalmically acceptable carrier without co-administration of another active pharmaceutical ingredient, wherein the pharmaceutical composition comprises 0.001% to 20% (by weight) Ivermectin, and wherein the pharmaceutical composition adheres to the eyelid margin.

In yet another aspect, the present invention provides a pharmaceutical composition comprising: (a) an ophthalmically acceptable carrier; and (b) a therapeutically effective amount of a biologically active substance, appropriate for precise application on eyelid margin of a subject, wherein the pharmaceutical composition adheres to the eyelid margins.

In yet another aspect, the present invention provides a topical pharmaceutical composition comprising 0.001% to 20% (by weight) of Ivermectin, and methods for making the topical pharmaceutical composition.

In yet another aspect, the present invention relates to an article of manufacture comprising the topical pharmaceutical composition; and a container with the topical pharmaceutical composition contained therein.

In yet another aspect, the present invention relates to a kit useful for treating anterior blepharitis and posterior blepharitis in a subject in need thereof, or primary blepharitis in a subject in need thereof, or both. The kit comprises the topical pharmaceutical composition; and an ocular applicator.

BRIEF DESCRIPTION OF THE FIGURES

The foregoing summary, as well as the following detailed description of the invention, is better understood when read in conjunction with the appended drawings. For illustrating the invention, exemplary constructions of the invention are shown in the drawings. However, the invention is not limited to the specific methods and compositions disclosed herein. The description of a method step or a composition referenced by a numeral in a drawing is applicable to the description of that method step or composition shown by that same numeral in any subsequent drawing herein.

DETAILED DESCRIPTION OF THE INVENTION

It is to be understood that the invention is not necessarily limited in its application to the details set forth in the following description or exemplified by the examples. The invention is capable of other embodiments or of being practiced or carried out in various ways. Also, it is to be understood that the phraseology and terminology employed herein is for the purpose of description and should not be regarded as limiting.

The term "pharmaceutical composition" is used herein to refer to a composition that is employed to prevent, reduce in intensity, cure or otherwise treat a target condition or disease.

The terms "subject" or "patient" are used interchangeably to refer to a member of an animal species of mammalian origin, including but not limited to, mouse, rat, cat, goat, cow, sheep, horse, hamster, ferret, pig, dog, platypus, guinea pig, rabbit and a primate, such as, for example, a monkey, ape, or human.

The phrase "subject in need thereof" as used herein refers to a subject that (i) will be administered a topical pharmaceutical composition of the described invention; (ii) is applying the topical pharmaceutical composition of the described invention; or (iii) has applied the topical pharmaceutical composition of the described invention, unless the context and usage of the phrase indicates otherwise.

The term "topical" refers to administration of a pharmaceutical composition directly on a target tissue. The terms "topical administration" and "topically applying" are used interchangeably to refer to delivering a pharmaceutical composition of the described invention onto one or more eyelid margins. The pharmaceutical composition may be applied by pouring, dropping, or spraying, if a liquid; rubbing on, if an ointment, lotion, cream, gel, or the like; dusting, if a powder; spraying, if a liquid or aerosol composition; or by any other appropriate means. Topical administration generally provides a local rather than a systemic effect.

The term "treatment" or "treating" includes abrogating, substantially inhibiting, slowing or reversing the progression of a disease, condition or disorder, substantially ameliorating symptoms of a condition. The term "treatment" or "treating" as used herein further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s) or curing the disease.

The term "excipient" as used herein refers to any inactive ingredient that is added to the pharmaceutical composition of the described invention and that is not intended to exert therapeutic effects at the intended dosage, although it may act to improve product delivery. Additional characteristics of excipients can be found in the Guidance for Industry Nonclinical Studies for the Safety Evaluation of Pharmaceutical Excipients issued by the US Food and Drug Administration Center for Drug Evaluation and Research, herein incorporated by reference.

The term "adheres" or "adhere" as used herein refers to synonymous to the property "stick fast", or "adhesion". The term "adheres" or "adhered" as used herein further refers to binding or confined or contained or restricted or substantial attachment of the pharmaceutical composition to the eyelid margin(s) or a drug dosage form or pharmaceutical composition that is in contact with eyelid margin(s) and is retained on the surface of the eyelid margin(s). The term "adhere" does not imply any particular degree of sticking or bonding, nor does it imply any degree of permanency.

Inflammation as of yet unknown origin is responsible for the vast majority of cases of both anterior and posterior blepharitis. Blepharitis due to an identifiable cause such as bacterial infection, mite infestation, rosacea or other causes form a minority of the cases of blepharitis commonly seen in clinical practice. Therapeutically effective treatments for this condition are of very limited effectiveness and require long term treatment as this condition is most frequently chronic.

The present invention provides a method for the treatment of anterior and posterior blepharitis which may be of primary origin and secondary to other factors such as infections, infestations or rosacea. The invention provides a method for treating blepharitis which may be classified as primary blepharitis affecting the anterior and posterior parts of the lid margin.

In one aspect, the present invention provides a method for treating anterior blepharitis and posterior blepharitis in a subject in need thereof, comprising topically administering, precisely on the eyelid margin of the subject, a pharmaceutical composition comprising Ivermectin and an ophthalmically acceptable carrier without co-administration of another active pharmaceutical ingredient, wherein the pharmaceutical composition comprises 0.001% to 20% by weight Ivermectin, and wherein the pharmaceutical composition adheres to the eyelid margin.

In an embodiment, the method comprises identifying the subject with primary inflammatory blepharitis and topically applying the pharmaceutical composition containing a therapeutically effective amount of Ivermectin precisely on the margins of the eyelids. The pharmaceutical composition is such that precise application to the eyelid margin is possible. The pharmaceutical composition sets and adheres to the eyelid margin and is retained in place for periods long enough to ensure adequate therapeutic bioavailability of the Ivermectin.

In an embodiment, the pharmaceutical composition has the properties of adherence to the underlying tissues, water resistance and water proofing and durability in a situation where the eyelids are regularly brought together by the natural act of blinking.

In an embodiment, the pharmaceutical composition retains the active ingredient within the application so that the dispersion or dissolution in the tear film is minimal. In an embodiment, the pharmaceutical composition has resistance to dispersion, and is thereby retained on the eyelid margin. In another embodiment, the pharmaceutical composition has durability over the surface applied on, and wherein the pharmaceutical composition is insoluble in the tear film. The method is effective in reducing the symptoms and signs of primary inflammatory blepharitis and in the treatment of evaporative dry eye secondary to inflammatory blepharitis.

The present inventor has found that a therapeutically effective concentration of Ivermectin contained in a pharmaceutical composition specifically designed for application on the eyelid margin extending from the eyelash roots proximally to and including the orifices of the Meibomian glands distally are unexpectedly effective in the treatment of anterior blepharitis and posterior blepharitis, particularly primary anterior and posterior blepharitis. This is an unexpected outcome because Ivermectin is primarily regarded as an endectocide.

A therapeutically effective concentration is defined in the medical arts as the concentration of the active ingredient that relieves the symptoms and signs associated with that condition, and where such improvement is maintained for the longest length of time without causing toxic effects. Typically, it has been found in the clinical setting that a 1% by weight of the total composition of Ivermectin is adequate, but this concentration is provided by way of an example and is not limiting of the invention in any way.

The pharmaceutical composition is also unexpectedly effective in the treatment of evaporative dry eye which is the result of a lack of lipids secreted by the Meibomian glands causing the lipid layer of the tear film to become deficient. This results in more rapid evaporation of the aqueous layer of the tear film as the evaporation retarding effect of the lipid layer of the tear film is deficient.

Chronic inflammation leads to blockage of the orifices of the Meibomian glands and consequent dropout and death of the Meibomian glands. Blockage of the Meibomian glands results in less lipids being secreted into the tear film. The present invention is effective in the treatment of the chronic non-infectious or non-infestational processes that cause blockage of the Meibomian glands and thereby provides for a healthy tear film.

In an embodiment, the pharmaceutical composition has properties that will contain the application to the lid margin and prevent or minimize the spread of that pharmaceutical composition to adjacent tissues such as the surface of the eyeball and the conjunctival sac.

In an embodiment, the pharmaceutical composition settles quickly after application, and provides waterproofing and water resistant properties.

In another embodiment, the pharmaceutical composition has the property of retainability after application so that it is resistant to cracking or displacing on eyelid movement or during contact with external surfaces such as hands, pillows or such and also being washed away and diluted by the tear film.

Primary anterior and posterior blepharitis refers to a condition where there is inflammation of the eyelid margin including the roots of the eyelashes and the Meibomian glands which is not directly attributable to an identifiable cause such as infection, infestation, rosacea or other systemic conditions. Identification of primary and secondary blepharitis is well known in the art and can include examination with a slit lamp bio microscope, swabbing of the eyelid margins for microscopy and culture and examination of epilated eyelashes under the microscope for the presence of mites, mites which are mainly absent in primary blepharitis of inflammatory origin.

In an embodiment, an effective concentration of Ivermectin contained in the pharmaceutical composition is that which significantly reduces or totally removes the symptoms and signs associated with the condition. It can also include reduction or total removal of excess keratinization of the skin of the eyelid margin and thereby, facilitate reopening of blocked Meibomian glands. It also includes the restoration of the Meibomian gland secretions to that which is of normal consistency, viscosity and clarity. It also provides improvement of symptoms of dry eye.

In an embodiment, the pharmaceutical composition comprises about 0.001% to 20% by weight of Ivermectin. In an embodiment, the pharmaceutical composition comprises about 0.5% to 5% by weight of Ivermectin. In another embodiment, the pharmaceutical composition comprises about 1% by weight Ivermectin.

In another embodiment, the present method provides a rapid and sustained improvement of the condition without the addition or co-administration of other active pharmaceutical ingredients such as antibiotics or steroid. This action is independent of any known antibacterial effect and is due to the unexpectedly effective anti-inflammatory effect of Ivermectin. The inventor found that this anti-inflammatory effect significantly surpasses the effectiveness of the currently used treatments such as lid scrubs, topical antibiotics and steroids.

In another embodiment, the pharmaceutical composition is administered periodically. In an embodiment, the pharmaceutical composition is applied daily for 3 days and the treatment is repeated for 3 days again after 2 weeks. In most cases this is sufficient for a significant therapeutic effect. The treatment using this frequency can be repeated again if the condition recurs but this is necessary only in a relatively small number of cases. The intermittent dosage of the Ivermectin provides the benefit of a lower amount of Ivermectin use and thereby lowers the possibility of adverse effects.

In another embodiment, the topical application allows the Ivermectin to be applied directly and precisely on an eyelid margin of the subject, thus overcoming the problem associated with oral application of Ivermectin being partitioned into the various body compartments, consequently with low concentrations at the specific target site. The direct topical application of the pharmaceutical composition onto the affected area also minimises the risk of medication-related side effects in other parts of the body.

In another embodiment, a subject with anterior and posterior blepharitis is identified and the existing symptoms and signs noted. The pharmaceutical composition is applied by the practitioner using for example, slit lamp magnification to accurately identify the areas on the eyelid margin where the pharmaceutical composition is to be applied. A topical anaesthetic drop is applied in the lower conjunctival sac of the eye 5 to 10 minutes prior. Temporary anaesthetization will attenuate the lacrimal reflex thereby minimizing the production of tear fluid during the application process.

In another embodiment, the pharmaceutical composition is precisely administered on an eyelid margin with an ocular applicator, for example, pre-treated with, or containing, the topical composition. In an embodiment, the applicator is a swab, cosmetic pad, wipe, wipe stick, towelette, sponge, gauze, puff, wand, brush, or comb. In an embodiment, a sponge tipped applicator or a brush is used to accurately apply the pharmaceutical composition as an adhesive film or coating extending from and including the orifices of the Meibomian glands distally to the eyelash roots and skin proximally. The eyelid is reflected away manually from contact with the eyeball during application. Care is taken to prevent efflux of the formulation into the conjunctival sac and to prevent contact with the eyeball.

In another embodiment, the pharmaceutical composition is applied on the entire length of the eyelid margin from the lateral canthus to but not including the puncta. The pharmaceutical composition is applied on both the upper eyelid 101 and the lower eyelid 105 margins. The eyelid margins may be further dried with a dry sponge or a swab before application. Drying the lid margin surface facilitates adhesion of the formulation.

In an embodiment, under a slit lamp or other suitable magnification, the eyelid is manually reflected away from the eyeball by the practitioner. Using a suitable sponge tipped applicator or a brush dipped into the pharmaceutical composition, it is applied on the lid margin with any excess composition wiped away.

The pharmaceutical composition is applied as a film precisely along the length of the lid margin with the applicator just covering the openings of the Meibomian glands but taking care as to not further extend the composition into the mucosal surface. The pharmaceutical composition is extended proximally to cover the lash roots and the skin area in between. The lid is held reflected away from the eyeball until the pharmaceutical composition sets and dries in place. The pharmaceutical composition takes the form of an adhesive film or coating on the lid margin. This procedure is repeated for all the 4 eyelid margins. The administration of the pharmaceutical composition results in enhanced meibum production.

In an embodiment, the application is left in place for about 6 to 12 hours and removed, for example, with a sponge tipped swab stick or a similar device dipped in a solution for specific use on the lid margin such as Blephagel or Blephacare. Care should be taken during removal so that the wiping action points away from the eyeball to prevent inadvertent efflux of the formulation into the conjunctival sac.

In another embodiment, the pharmaceutical composition is applied by the subject themselves using, for example, a concave magnifying mirror. The pharmaceutical composition according to the invention is formulated to not cause eye irritation. This invention therefore allows patients to apply such medication themselves, without having to go to a clinic. Patients may be able to continuously repeat the dosage over a period of time, so as to ensure a lower risk of recurrence of blepharitis.

Various embodiments of the pharmaceutical composition having the requirement of setting and drying on application, waterproof or water resistance, ability to be applied accurately over a small space, durability and retention are known to those skilled in the art.

In another embodiment, the ophthalmically acceptable carrier comprises at least one ophthalmically acceptable excipient.

In another embodiment, the pharmaceutical composition comprises one or more of the following ingredients: sterile distilled water, Ivermectin, chelating agent, humectant, gum/thickener, anionic emulsifier, non-ionic emulsifier, water proofing agent, base, preservative, antioxidant, and pH adjuster.

In another embodiment, the pharmaceutical composition comprises Ivermectin in the range of about 0.5% to 5% by weight. In an embodiment, the pharmaceutical composition comprises about 1% by weight Ivermectin.

In another embodiment, the pharmaceutical composition comprises water in the range of about 0.1%-99.0% by weight. In another embodiment, the pharmaceutical composition comprises water in the range of about 50% to 75% by weight.

In another embodiment, the pharmaceutical composition further comprises a chelating agent in the range of about 0.1% to 5.0% by weight. In an embodiment, the pharmaceutical composition comprises a chelating agent in the range of about 0.08% to 0.2% by weight. The chelating agent is selected from, but not limited to, disodium EDTA, sodium phytate, and tetrasodium EDTA.

In another embodiment, the pharmaceutical composition further comprises a humectant in the range of about 0.5% to 5.0% by weight. In an embodiment, the pharmaceutical composition comprises a humectant in the range of about 1.5% to 3% by weight. The humectant is selected from, but not limited to, glycerine, propanediol, and propylene glycol.

In another embodiment, the pharmaceutical composition comprises gums or thickeners in the range of about 0.2% to 2.0% by weight. In an embodiment, the pharmaceutical composition comprises gums or thickeners in the range of about 0.1% to 1% by weight. The gums or thickeners is selected from, but not limited to, guar gum, hydroxyethyl cellulose, xanthan gum and veegumgel.

In another embodiment, the pharmaceutical composition comprises an anionic emulsifier in the range of about 0.3% to 3.0% by weight. In an embodiment, the pharmaceutical composition comprises an anionic emulsifier in the range of about 0.35% to 0.75% by weight. The anionic emulsifier is selected from, but not limited to, glyceryl stearate citrate, sodium stearoyl glutamate, and glyceryl stearate SE.

In another embodiment, the pharmaceutical composition comprises a non-ionic emulsifier in the range of about 3% to 10% by weight. In an embodiment, the pharmaceutical composition comprises a non-ionic emulsifier in the range of about 4% to 8% by weight. The non-ionic emulsifier is selected from, but not limited to, cetearyl alcohol, cetearyl alcohol/polysorbate 60, and glyceryl stearate/PEG-100 stearate.

In another embodiment, the pharmaceutical composition comprises a waterproofing agent in the range of about 5% to about 12% by weight. In an embodiment, the pharmaceutical composition comprises a waterproofing agent in the range of about 6% to 10% by weight. The waterproofing agent is selected from, but not limited to, bis-stearyl ethylenediamine, neopentyl glycol, stearyl hydrogenated dimer dilinoleatecopolymer (Sylvaclear C75V), and ethylenediamine/hydrogenated dimer dilinoleate copolymer bis-di-$C_{14-18}$ alkyl amide (Sylvaclear A200V). The addition of a waterproofing agent provides water resistance and waterproofing qualities to the pharmaceutical composition.

In another embodiment, the pharmaceutical composition comprises a base in the range of about 10% to 45% by weight. In an embodiment, the pharmaceutical composition comprises a base in the range of about 6% to 10% by weight. The base is selected from, but not limited to, silicone oils such as dimethicone 350 cps, dimethicone 500 cps, dimethicone 1000 cps. Dimethicone has pore penetrating property, thereby providing adequate penetration of the pharmaceutical composition through the orifices of the Meibomian gland to deliver the active ingredient into the gland. The base may also contain other compounds such as ammonium acrylates copolymer and sodium acrylates copolymer that provide added waterproofing qualities to the pharmaceutical composition.

In another embodiment, the pharmaceutical composition further comprises a preservative in the range of about 0.5% to 3% by weight. In an embodiment, the pharmaceutical composition comprises a preservative in a range of about 1% to 1.75% by weight. The preservative is selected from, but not limited to, phenoxyethanol and caprylyl glycol.

In another embodiment, the pharmaceutical composition comprises an antioxidant in the range of about 0.01% to 0.5% by weight. In an embodiment, the pharmaceutical composition comprises an antioxidant in the range of about 0.025% to 0.3% by weight. The antioxidant is, but not limited to, tocopherol D-alpha 50%.

In another aspect, the present invention provides a method for treating primary blepharitis in a subject in need thereof, comprising topically administering, once daily for 3 days and repeated once daily for 3 days after 2 weeks, precisely on an eyelid margins of the subject, a pharmaceutical composition comprising Ivermectin and an ophthalmically acceptable carrier without co-administration of another active pharmaceutical ingredient, wherein the pharmaceutical composition comprises about 0.001% to 20% by weight Ivermectin, and wherein the pharmaceutical composition adheres to the eyelid margin.

In another aspect, the present invention provides a pharmaceutical composition comprising: (a) an ophthalmically acceptable carrier; and (b) a therapeutically effective amount of a biologically active substance, appropriate for precise application on an eyelid margin of a subject, wherein the pharmaceutical composition adheres to the eyelid margins.

In an embodiment, the ophthalmically acceptable carrier comprises at least one ophthalmically acceptable excipient.

In an embodiment, the biologically active substance can be any beneficial agent that can be delivered to the lid margin. In an embodiment, the biologically active substance is selected from a group consisting of antiparasites, steroids, antibiotics, anti-inflammatory agents, anti-neoplastic agents, anti-virals, growth factors, serums.

In an embodiment, the pharmaceutical composition has adherence properties and resistance to dispersion, which allows the pharmaceutical composition to be retained in place for periods sufficient to ensure adequate bioavailability of the biologically active substance.

In another embodiment, the pharmaceutical composition containing a therapeutically effective amount of the biologically active substance is applied precisely on the margins of the eyelids of the subject identified with primary inflammatory blepharitis.

In another embodiment, the ophthalmically acceptable excipient is one or more of the following: sterile distilled water, chelating agent, humectant, gum/thickener, anionic emulsifier, non-ionic emulsifier, water proofing agent, base, preservative, antioxidant, and a pH adjuster.

In another embodiment, the pharmaceutical composition comprises water in the range of about 0.1%-99.0% by weight. In an embodiment, the pharmaceutical composition comprises water in the range of about 50% to 75% by weight.

In another embodiment, the pharmaceutical composition comprises a chelating agent in the range of about 0.1% to 5.0% by weight. In an embodiment, the pharmaceutical composition comprises a chelating agent in the range of about 0.08% to 0.2% by weight. The chelating agent is selected from, but not limited to, disodium EDTA, sodium phytate, and tetrasodium EDTA.

In another embodiment, the pharmaceutical composition comprises a humectant in the range of 0.5%-5.0% by weight. In an embodiment, the pharmaceutical composition comprises a humectant in the range of about 1.5% to 3% by weight. The chelating agent is selected from, but not limited to, glycerine, propanediol, and propylene glycol.

In another embodiment, the pharmaceutical composition comprises gums or thickeners in the range of about 0.2% to 2.0% by weight. In an embodiment, the pharmaceutical composition comprises gums or thickeners in the range of about 0.1% to 1% by weight. The gums or thickeners is selected from, but not limited to, guar gum, hydroxyethyl cellulose, xanthan gum, and veegumgel.

In another embodiment, the pharmaceutical composition comprises an anionic emulsifier in the range of about 0.3% to 3.0% by weight. In an embodiment, the pharmaceutical composition comprises anionic emulsifier in the range of about 0.35% to 0.75% by weight. The anionic emulsifier is selected from, but not limited to, glyceryl stearate citrate, sodium stearoyl glutamate, and glyceryl stearate SE.

In another embodiment, the pharmaceutical composition comprises a non-ionic emulsifier in the range of about 3% to 10% by weight. In an embodiment, the pharmaceutical composition comprises a non-ionic emulsifier in the range of 4% to 8% by weight. The non-ionic emulsifier is selected from, but not limited to, cetearyl alcohol, cetearyl alcohol/polysorbate 60, glyceryl stearate/PEG-100 stearate.

In another embodiment, the pharmaceutical composition further comprises a waterproofing agent in the range of about 5% to about 12% by weight. In an embodiment, the pharmaceutical composition comprises a waterproofing agent in the range of about 6% to 10% by weight. The waterproofing agent is selected from, but not limited to, bis-stearyl ethylenediamine, neopentyl glycol, stearyl hydrogenated dimer dilinoleatecopolymer (Sylvaclear C75V) or ethylenediamine/hydrogenated dimer dilinoleate copolymer bis-di-$C_{14-18}$ alkyl amide (Sylvaclear A200V). The addition of a waterproofing agent provides additional water resistance and waterproofing qualities to the pharmaceutical composition.

In another embodiment, the pharmaceutical composition comprises a base in the range of about 10% to 45% by weight. In an embodiment, the pharmaceutical composition comprises a base in the range of about 6% to 10% by weight. The base is selected from, but not limited to, silicone oils such as dimethicone 350 cps, dimethicone 500 cps, dimethicone 1000 cps. Dimethicone has a pore penetrating property, thereby allowing an adequate penetration of the pharmaceutical composition through the orifices of the Meibomian gland to deliver the active ingredient into the gland. The base may also contain other compounds such as ammonium acrylates copolymer and sodium acrylates copolymer that provide added waterproofing qualities to the pharmaceutical composition.

In another embodiment, the pharmaceutical composition further comprises a preservative in the range of about 0.5% to 3% by weight. In an embodiment, the pharmaceutical composition comprises a preservative in the range of about 1% to about 1.75% by weight. The preservative can be selected from, but not limited to, phenoxyethanol, and caprylyl glycol.

In another embodiment, the pharmaceutical composition comprises an antioxidant in the range of about 0.01% to 0.5% by weight. In an embodiment, the pharmaceutical composition comprises an antioxidant in the range of about 0.025% to 0.3% by weight. The antioxidant is, but not limited to, Tocopherol D-alpha 50%.

In another embodiment, the pharmaceutical composition has a pH between 5 and 8. In an embodiment, the pharmaceutical composition has a pH between 6 and 7.

In another aspect, the present invention provides a topical pharmaceutical composition comprising about 0.001% to 20% by weight of Ivermectin, and methods for making the topical pharmaceutical composition. In embodiments, the pharmaceutical composition is a solution, suspension, salve, spray, stick, lotion, gel, paste, balm, foam, mousse, scrub or cleanser (e.g., shampoo or soap), cream, or ointment. Soaps may be solid, such as a bar, liquid, or semi-solid.

In another aspect, the present invention relates to an article of manufacture comprising the topical pharmaceutical composition, and a container with the topical pharmaceutical composition contained therein. In embodiments, the container is a collapsible or non-collapsible tube, bag, packet, blister, strip, ampoule, vial, bottle, can, or jar.

In another aspect, the present invention relates to a kit useful for treating anterior blepharitis and posterior blepharitis in a subject in need thereof, or primary blepharitis in a subject in need thereof, or both. The kit comprises the topical pharmaceutical composition, and an ocular applicator. Optionally, the applicator may be pre-treated with, or contain the topical pharmaceutical composition. The kit may further include a container containing the composition. The kit may further include instructions (e.g., printed or digital instructions) for treating anterior blepharitis and posterior blepharitis in a subject in need thereof, or primary blepharitis in a subject in need thereof, by topically administering the composition precisely on an eyelid margin of the subject.

Ophthalmic preparations are to be prepared such that it is tolerated by the ocular tissues and made in accordance with sterile compounding practices as detailed in the U.S. Pharmacopeia National Formulary 2019 UPS42-NF37 by the United States Pharmacopeial Convention.

A clinic based application of topical Ivermectin for the treatment of inflammatory blepharitis has been successful; both for cases where Demodex species were not isolated which constituted the majority of cases of Blepharitis treated, and the smaller number of cases where Demodex species were isolated. Most of these were cases with long-standing disease which had been unresponsive to a wide range of currently accepted treatment modalities. More than 95% had full relief of symptoms and a remarkable reduction in signs of inflammation of the lid margins. 87% of the cases required only 1 treatment cycle for marked improvement or complete remission of symptoms. A significant number also showed re-opening of previously closed Meibomian gland orifices, re-opening of previously occluded Meibomian gland orifices and the reappearance of normal Meibomian gland secretions. The majority of the cases where dry eye symptoms were present also showed remarkable improvement.

EXAMPLES

All the percentages recited herein refer to weight percent, unless otherwise indicated. The following non-limiting examples serve to illustrate embodiments of the present invention.

Example 1

Method:

Ingredients of Phase A (water, Ivermectin, and disodium EDTA) were added and stirred (until dissolution). Phase B (slurry of xanthan gum in propanediol) was added to the mixture of Phase A under low shear until a homogenous gel was formed. The homogenous gel was heated to 80° C.

Ingredients of Phase C (glyceryl stearate citrate, cetearyl alcohol, bis-stearyl ethylenediamine, neopentyl glycol, stearyl hydrogenated dimer dilinoleate copolymer) were combined and heated to 80° C. Ingredients of Phase D (dimethicone 350 cps and dimethicone 500 cps, Ammonium and Sodium Acrylates Copolymer) were combined, and added to Phase C mixture, and stirred until homogenous.

The mixture obtained by adding Phase C and D were added to the mixture obtained by added Phase A and B and stirred vigorously until homogenous.

The mixture was allowed to cool below 40° C. and then, ingredients of Phase E (phenoxyethanol, caprylyl glycol, Tocopherol-D-alpha 70% Qs pH adjuster) were added and stirred until homogenous. The pH was adjusted to between 6 and 7.

The ingredients and amounts used in Example 1 are summarized in Table 1.

TABLE 1

| PHASE | % W/W | INGREDIENT |
|---|---|---|
| A | 62.35 | WATER |
| A | 1.0 | IVERMECTIN |
| A | 0.1 | DISODIUM EDTA (CHELATING AGENT) |
| B | 2.0 | PROPANEDIOL (HUMECTANT) |

TABLE 1-continued

| PHASE | % W/W | INGREDIENT |
|---|---|---|
| B | 0.20 | XANTHAN GUM (THICKENER) |
| C | 0.50 | GLYCERYL STEARATE CITRATE (ANIONIC EMULSIFIER) |
| C | 5.0 | CETEARYL ALCOHOL (NON-IONIC EMULSIFIER) |
| C | 8.0 | BIS-STEARYL ETHYLENEDIAMINE, NEOPENTYL GLYCOL, STEARYL HYDROGENATED DIMER DILINOLEATE COPOLYMER (Sylvaclear C75V) (WATERPROOFING AGENT) |
| D | 4.75 | DIMETHICONE 350 cps (BASE) |
| D | 4.75 | DIMETHICONE 500 cps (BASE) |
| D | 5.00 | AMMONIUM ACRYLATES COPOLYMER (BASE) |
| D | 5.00 | SODIUM ACRYLATES COPOLYMER (BASE) |
| E | 1.30 | PHENOXYETHANOL, CAPRYLYL GLYCOL (PRESERVATIVE) |
| E | 0.05 | TOCOPHEROL-D-ALPHA 70% Qs pH ADJUSTER |

Example 2

Method:

Ingredients of Phase A (deionized water and veegum) were mixed with high shear mixing until smooth.

Phase B (triethanolamine and propylene glycol) was added to the mixture of Phase A and mixed until uniform.

Phase C (xanthan gum, Tocopherol-D-alpha 70%) was added to the above mixture of Phase A and B, and then mixed until uniform using high shear mixing.

Phase D (stearic acid, glyceryl stearate, oleyl alcohol) and Phase E (dimethicone 350 CPS, dimethicone 1000 CPS) were melted to 75° C.±5° C. in separate containers and then mixed with high shear mixing.

The mixture of Phases D, E and the mixture Phases A, B, C were mixed together with high shear and cooled to 35° C.±5° C.

Phase F (Ivermectin sterile micronized) was then added to the above mixture, mixed completely and stored in sterile containers.

The ingredients and amounts used for Example 2 are summarized in Table 2.

TABLE 2

| PHASE | % W/W | INGREDIENT |
|---|---|---|
| A | 72.5 | DEIONIZED WATER |
| A | 1.0 | VEEGUM |
| B | 1.40 | TRIETHANOLAMINE |
| B | 10.00 | PROPYLENE GLYCOL |
| C | 0.5 | XANTHAN GUM |
| C | 1.5 | TOCOPHEROL-D-ALPHA 70% |
| D | 2.80 | STEARIC ACID |
| D | 0.80 | GLYCERYL STEARATE |
| D | 0.50 | OLEYL ALCOHOL |
| E | 4.0 | DIMETHICONE 350 CPS |
| E | 4.0 | DIMETHICONE 1000 CPS |
| F | 1.0 | IVERMECTIN STERILE MICRONIZED |

Example 3

Method:

Ingredients of Phase A (deionized water and veegum) were mixed with high shear mixing until smooth.

Phase B (triethanolamine and propylene glycol) was added to the mixture of Phase A and mixed until uniform.

Phase C (xanthan gum, Tocopherol-D-alpha 70%) was added to the above mixture of Phase A and B, and then mixed until uniform using high shear mixing.

Phase D (stearic acid, glyceryl stearate, oleyl alcohol) and Phase E (carnauba wax, white bees wax) were melted to 75° C.±5° C. in separate containers and then, mixed with high shear mixing.

The mixture of Phases D, E and the mixture Phases A, B, C were mixed together with high shear and cooled to 35° C.±5° C.

Phase F (Ivermectin sterile micronized) was then added to the above mixture, mixed completely and stored in sterile containers.

The ingredients and amounts used for Example 3 are summarized in Table 3.

TABLE 3

| PHASE | % W/W | INGREDIENT |
|---|---|---|
| A | 72.5 | DEIONIZED WATER |
| A | 1.0 | VEEGUM |
| B | 1.40 | TRIETHANOLAMINE |
| B | 10.00 | PROPYLENE GLYCOL |
| C | 0.5 | XANTHAN GUM |
| C | 1.5 | TOCOPHEROL-D-ALPHA 70% |
| D | 2.80 | STEARIC ACID |
| D | 0.80 | GLYCERYL STEARATE |
| D | 0.50 | OLEYL ALCOHOL |
| E | 4.0 | CARNAUBA WAX |
| E | 4.0 | WHITE BEESWAX |
| F | 1.0 | IVERMECTIN STERILE MICRONIZED |

The above pharmaceutical compositions are presented as examples only and are not limitative of the invention. Variations of the formulation as may be formulated by a person of ordinary skill in the art to precisely apply the composition on the eye lid margins from the anterior most eyelashes and the adjacent skin to include the keratinized skin from the eye lashes to the mucocutaneous junction on the lid margin and including the orifices of the Meibomian glands. These pharmaceutical compositions will have in common, the properties of setting and drying quickly, forming a film like structure on the eyelid margins, water resistance and waterproofing, resistance to dispersion and dissolution in the tear film and durability to prevent it being wiped away or washed away unintentionally. The pharmaceutical compositions will be able to penetrate through the Meibomian gland orifices and into the ampulla of the gland duct.

It will be readily apparent to those skilled in the art that further changes and modifications in actual implementation of the concepts described herein can easily be made or may be learned by practice of the invention, without departing from the spirit and scope of the invention as defined by the following claims.

I claim:

1. A method for treating primary blepharitis, wherein the primary blepharitis is primary anterior blepharitis or primary posterior blepharitis, the method comprising:
    topically administering, to a subject in need thereof, a pharmaceutical composition comprising ivermectin and an ophthalmically acceptable carrier, without co-administration of another active pharmaceutical ingredient, wherein the route of administration comprises topically applying the pharmaceutical composition on an eyelid margin extending from the eyelash roots proximally to and including the orifices of the meibomian glands distally of the subject, wherein the pharmaceutical composition is configured to adhere to the eyelid margin, wherein the primary blepharitis is not related to or for the treatment of bacterial infection, mite infestation, rosacea or psoriasis, and wherein the pharmaceutical composition comprises about 0.5% to about 5% by weight ivermectin.

2. The method according to claim 1, wherein the pharmaceutical composition has resistance to dispersion or dissolution in a tear film.

3. The method according to claim 1, wherein the primary anterior blepharitis and the primary posterior blepharitis are associated with meibomian gland disease and/or dry eye disease.

4. The method according to claim 1, wherein the topical administration is a periodic administration.

5. The method according to claim 1, wherein the pharmaceutical composition is applied once daily for 3 days in a first cycle; and applied again for 3 days in a second cycle, wherein the second cycle starts 2 weeks after completion of the first cycle.

6. The method according to claim 1, wherein the pharmaceutical composition comprises about 1% by weight ivermectin.

7. The method according to claim 1, wherein the pharmaceutical composition further comprises one or more ingredients selected from the group consisting of a chelating agent, humectant, gum/thickener, emulsifier, waterproofing agent, base, preservative, antioxidant, pH adjuster, and water.

8. The method according to claim 7, wherein the chelating agent is disodium ethylenediaminetetraacetate.

9. The method according to claim 1, wherein the pharmaceutical composition further comprises water in the range of about 50% to 75% by weight.

10. The method according to claim 1, wherein the administration of the pharmaceutical composition results in enhanced meibum production.

11. The method according to claim 1, further comprising administering the pharmaceutical composition on an eyelid margin with an applicator.

12. The method according to claim 1, further comprising administering the pharmaceutical composition on the entire length of the eyelid margin and on both upper and lower eyelid margins.

13. The method according to claim 1, wherein the subject is one of a mouse, rat, cat, goat, cow, sheep, horse, hamster, ferret, pig, dog, platypus, guinea pig, rabbit, ape, monkey and human.

14. A method for treating primary blepharitis, wherein the primary blepharitis is primary anterior blepharitis or primary posterior blepharitis, the method comprising:
    topically administering, to a subject in need thereof, a pharmaceutical composition comprising ivermectin and an ophthalmically acceptable carrier, without co-administration of another active pharmaceutical ingredient, wherein the route of administration comprises topically applying the pharmaceutical composition on an eyelid margin extending from the eyelash roots proximally to and including the orifices of the meibomian glands distally of the subject, wherein the pharmaceutical composition is configured to adhere to the eyelid margin, wherein the primary blepharitis is not related to or for the treatment of bacterial infection, rosacea or psoriasis, and wherein the pharmaceutical composition is:
    applied once daily for 3 days in a first cycle; and
    applied again for 3 days in a second cycle, wherein the second cycle starts 2 weeks after completion of the first cycle.

15. The method according to claim 14, wherein the pharmaceutical composition comprises about 0.001% to 20% by weight ivermectin, and wherein the ophthalmically acceptable carrier comprises one or more ingredients selected from the group consisting of: chelating agent, humectant, thickener, emulsifier, waterproofing agent, base, preservative, antioxidant, pH adjuster, and water.

\* \* \* \* \*